(12) United States Patent
Lutje Spelberg et al.

(10) Patent No.: US 7,695,942 B2
(45) Date of Patent: Apr. 13, 2010

(54) ENZYMATIC CONVERSION OF EPOXIDES

(75) Inventors: Jeffrey Harald Lutje Spelberg, Groningen (NL); Dick Barend Janssen, Roden (NL)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 11/833,933

(22) Filed: Aug. 3, 2007

(65) Prior Publication Data

US 2008/0220485 A1 Sep. 11, 2008

Related U.S. Application Data

(63) Continuation of application No. 10/302,788, filed on Nov. 22, 2002, now abandoned, which is a continuation of application No. PCT/NL01/00403, filed on May 23, 2001.

(30) Foreign Application Priority Data

May 25, 2000 (EP) .................................. 00201874

(51) Int. Cl.
C12P 7/02 (2006.01)
(52) U.S. Cl. ..................................... 435/155; 435/232
(58) Field of Classification Search .................. 435/155, 435/232
See application file for complete search history.

(56) References Cited

U.S. PATENT DOCUMENTS 5,210,031 A    5/1993   Nakamura et al.

FOREIGN PATENT DOCUMENTS

| EP | 0879890 A1 | 5/1997 |
| JP | 04-278089 A | 10/1992 |
| JP | 10-210981 A | 8/1998 |
| JP | 10210981 A | 8/1998 |
| WO | WO 98/53081 A1 | 11/1998 |

OTHER PUBLICATIONS

Opposition to EP 1 287 155 B1 dated May 23, 2007.
PCT International Search Report from PCT/NL01/00403 dated Aug. 21, 2001.
Archer, 1997, "Epoxide Hydrolases as Asymmetric Catalysts," Tetrahedron, Elsevier Science, 53(46):15617-15662.
Assis et al., May 1998, "Synthesis of Chiral Epihalohydrins Using Haloalcohol Dehalogenase A from Arthobacter Erithii H10a," Enzym Microb. Technol. 22:545-551.
Besse et al., 1994, "Enantioselective Synthesis of Both Enantiomers of Cathinone via the Microbiological Reduction of 2-Azido-1-phenyl-1-propanone," J. Org. Chem., 59(26):8288-8291.
Boyd et al., 1996, "Stereoselective Dioxygenase-Catalysed Benzylic Hydroxylation of Prochiral Methylene Groups in the Chemoenzymatic Synthesis of Enantiopure Vicinal Aminoindanols," Tetrahedron: Asymmetry, Elsevier Science, 7(6):1559-1562.

Foelsche et al., 1990, "Lipase-Catalyzed Resolution of Acyclic Amino Alcohol Precursors," J. Org. Chem., 55(6):1749-1753.
Kasai et al., 1998, "Chiral C3 Epoxides and Halohydrins: Their Preparation and Synthetic Application," J. Molec. Cat. B: Enzymatic, 4:237-252.
Larrow et al., 1996, "Kinetic Resolution of Terminal Epoxides via Highly Regioselective and Enantioselective Ring Opening with TMSN, An Efficient, Catalytic Route to 1,2-Amino Alcohols," J. Am. Chem. Soc., 118(31):7420-7421.
Lewis et al., 1999, "Cloning and Nucleotide Sequence of the Haloalcohol Dehalogenase B Gene from Agrobacterium Tumefaciens," Database Accession No. Q9WWB6. XP002152213.
Lutje Spelberg et al., 2001, "Highly Enantioselective and Regioselective Biocatalytic Azidolysis of Aromatic Epoxides," Org. Lett., 3(1):41-43.
Lutje Spelberg et al., 1998, "Enantioselectivity of a Recombinant Epoxide hydrolase from Agrobacterium Radiobacter," Tetrahedron: Asymmetry, Elsevier Science, 9(3):459-466.
Lutje Spelberg et al., 1999, "A Tandem Enzyme Reaction to Produce Optically Active Halohydrins, Epoxides and Diols," Tetrahedron: Asymmetry, 10:2863-2870.
Martinez et al., 1995 "Highly Enantioselective Ring Opening of Epoxides Catalyzed by (salen)Cr(III)Complexes," J. Am. Chem. Soc., 117(21):5897-5898.
Mischitz et al., 1994 "Asymmetric Opening of an Epoxide by Azide Catalyzed by an Immobilized Enzyme Preparation from Rhodococcus sp.," Tetrahedron Letters, 35(1):81-84.
Nakamura et al., 1994, "A New Enzymatic Synthesis of (R)-γ-Chloro-β-Hydroxybutyronitrile," Tetrahedron, Elsevier Science, 50(41):11821-11826.
Nakamura et al., 1994, "Characterization of a Novel Enantioselective Halohydrin Hydrogen-Halide-Lyase," Appl. Biochem. Biotechnol. 60(4):1297-1301.
Nakamura et al., 1992, "Resolution and Some Properties of Enzymes Involved in Enantioselective Transformation of 1,3-Dichloro-2-Propanol to (R)-3-Chloro-1,2-Propanediol by Corynebacterium sp. Strain N-1074," J. Bacteriol., 174(23):7613-7619.
Poelarends et al., Apr. 1999, "Degradation of 1,2-Dibromoethane by Mycobacterium sp. Strain GP1," J. Bacteriol., 181(7):2050-2058.
Rink et al., Jun. 1997, "Primary Structure and Catalytic Mechanism of the Epoxide Hydrolase from Agrobacterium Radiobacter AD1," J. Biol. Chem., 272(23):14650-14657.
SEQ ID No. 2 Comparison to Accession No. AAW69435 in JP1020981 A1, Aug. 11, 1998.
Straathof et al., Dec. 1997, "The Enantiomeric Ratio: Origin, Determination and Prediction," Enzyme Microb. Technol., 21:559-571.
Van Den Wijngaard et al., Jan. 1991, "Purification and Characterization of Haloalcohol Dehalogenase from Arthrobacter sp. Strain AD2," J. Bacteriol., 173(1):124-129.
Yu et al., 1994, "Cloning of Two Halohydron Hydrogen-Halide-Lyase Genes of Corynebacterium sp. Strain N-1074 and Structural Comparison of the Genes and Gene Products," Biosci., Biotechnol., Biochem. 58(8):1451-1457.

(Continued)

Primary Examiner—Tekchand Saidha
(74) Attorney, Agent, or Firm—Dechert LLP

(57) ABSTRACT

The invention relates to a process for converting an epoxide to an alcohol. The process according to the invention is enzymatically catalyzed and highly enantioselective and regiospecific.

28 Claims, No Drawings

OTHER PUBLICATIONS

Opposition of Ep 1287155—Patent Proprietor's Response to Opposition, May 29, 2008.
Opposition of EP 1287155—Declaration of Jeffrey Lutje Spelberg.
Opposition of EP 1287155—Preliminary Non-Binding Opinion of Opposition Division of European Patent Office, Feb. 27, 2009.
Opposition of EP 1287155—Reply by Opponent, Jul. 16, 2009.
Opposition of EP 1287155—Written Submission by Patent: Proprietor, Jul. 24, 2009.
PCT/NL01/00403—PCT International Preliminary Examination Report, Aug. 30, 2002.
PCT/NL01/00403—PCT Written Opinion, May 29, 2002.
PCT/NL01/00403—Response to Written Opinion, Aug. 13, 2002.
PCT/NL01/00403—Response to Written Opinion, Mar. 19, 2002.
Jorns, M. S., 1980, "Studies on the Kinetics of Cyanohydrin Synthesis and Cleavage by the Flavoenzyme Oxynitrilase," *Biochim Biophy. Acta* 613:203-209.
Hasnoui-Dijoux et al., 2008, "Catalytic Promiscuity of Halohydrin Dehalogenase and its Application in Enantioselective Epoxide Ring Opening," *ChemBioChem* 9:1048-1051.

Wells, P. R., "Linear Free Energy Relationships," *Chem Rev.* 63:171-219.
Fringuelli et al., 1999, "Ring Opening of Epoxides with Sodium Azide in Water: A Regioselective pH-Controlled Reaction," *J Org. Chem.* 63:6094-6096.
Guy et al., 1992, "Selective Ring Opening Reaction of Styrene Oxide with Lithium Azide in the Presence of Cyclodextrins in Aqueous Media," *Tetrahedron Asymmetry* 3(2):247-250.
De Vries et al., *Biocatalysis* 2005, St Petersburg, Russia, Abstract Presentation.
Van Hylckama Vlieg et al., 2001, "Halohydrin Dehalogenases Are Structurally and Mechanistically Related to Short-Chain Dehydrogenases/Reductases," *J Bact.* 183(17:5058-5066.
Elenkov et al., 2004, "Enantioselective Ring Opening of Epoxides with Cyanide Catalyzed by Halohydrin Dehalogenases: A New Approach to Non-Racemic β-Hydroxy Nitriles," *Adv. Synth. Catal.* 348:579-585.
Lutje Spelberg et al., 2004, "Enzymatic dynamic kinetic resolution of epihalohydrins," *Tetrahedron: Asymmetry* 15:1095-1102.

ENZYMATIC CONVERSION OF EPOXIDES

1. CROSS REFERENCE TO RELATED APPLICATIONS

This application is a continuation of U.S. application Ser. No. 10/302,788, filed Nov. 22, 2002, pending, which is a continuation of International Patent Application No. PCT/NL01/00403, filed May 23, 2001, which claims priority to European Patent Application No. EP00201874.5, filed May 25, 2000, the content of each application is hereby incorporated by reference.

2. DESCRIPTION

The invention relates to a process for converting an epoxide to an alcohol. More specifically, the invention relates to an enzymatic process for converting an epoxide to an alcohol by nucleophilic substitution.

A reaction wherein an epoxide is converted to an alcohol by nucleophilic substitution may be depicted as follows:

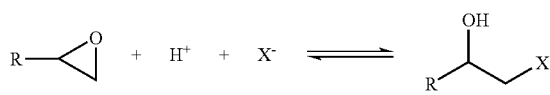

In this reaction scheme, R may represent a wide range of groups, such as various substituted or unsubstituted alkyl groups, whereas X represents a nucleophile. The product of this conversion may be a very useful building block in the preparation of various fine chemicals, such as certain pharmaceutical products. The reaction may produce two different enantiomers. As the products are often used for applications wherein enantiomeric purity is of great importance, many attempts to find enantioselective ways of carrying out this reaction have been reported.

An example of such a reaction is the enantioselective ring opening of an epoxide by an azide anion ($N_3^-$), which may be referred to as an azidolysis. The product of the reaction, an optically active azido alcohol is a precursor for biologically active pharmaceuticals such as amino alcohols. A highly enantioselective azidolysis of meso-epoxides and various terminal epoxides using chiral salen complexes has been described by the group of Jacobsen (Martinez et al., J. Am. Chem. Soc., 1995, 117, 5897; Farrow et al., J. Am. Chem. Soc., 1996, 118, 7420). Preparations of optically active aromatic azidoalcohols through a biocatalyzed reaction have also been reported: e.g., by reduction of an α-azidoketone (Bese et al., J. Org. Chem., 1994, 59, 8288), lipase catalyzed resolution (Foelsche et al., J. Org. Chem., 1990, 55, 1749), or monohydroxylation (Boyd et al., Tetrahedron: Asymmetry, 1996, 7, 1559).

The reverse reaction, i.e., the formation of an epoxide from, e.g., a haloalcohol, using an enzymatically catalyzed reaction, has been given much attention in the literature, particular using halohydrin dehalogenases. All these reactions involved aliphatic halohydrins, such as 1,3-dihalopropanol, 2,3-dihalopropanol, and 3-halo-1,2-propanediol, to produce optically pure halohydrins and epoxides (Kasai et al., J. Mol. Cat:B, 1998, 4, 237). Generally, a halohydrin dehalogenase (also referred to as halohydrin hydrogen-halide-lyase, halohydrin epoxidase or haloalcohol dehalogenase) catalyzes the ring-closure of a halohydrin to an epoxide. For a limited number of halohydrins, it has been described that a halohydrin dehalogenase may also catalyze the reverse reaction. The equilibrium of both reactions may be depicted as follows:

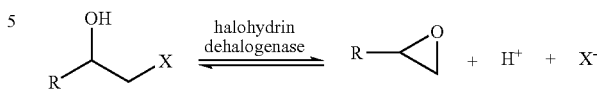

wherein R may be chosen from a wide range of groups, such as various substituted or unsubstituted aryl or alkyl groups, and wherein X represents a halogen such as bromide, chloride or iodide.

One example using a halohydrin dehalogenase and a nucleophile different from a halide has been described by Nakamura et al., Tetrahedron, 1994, 50, 11821. In this reaction, a halohydrin dehalogenase from *Corynebacterium* sp. Strain N-1074 was used to open an epoxide with cyanide to yield a β-hydroxy nitrile.

Asymmetric ring opening of an epoxide by azide has been described using a crude enzyme preparation from a *Rhodococcus* sp. (see Faber et al., Tetrahedron Letters, 1994, 35, 81). The enzyme responsible for the reaction is suggested to be an epoxide hydrolase rather than a halohydrin dehalogenase.

When compared to chemically catalyzed reactions, reactions catalyzed by use of enzymes involve the use of less (organic) solvents, or other reagents that might be environmentally suspect such as metal complexes and the like. For example, catalytic chemical azidolysis of epoxides is typically performed using environmentally unfriendly metals, such as chromium, cobalt or titanium complexes, in organic solvents, such as dichloromethane, acetonitrile or dimethylformamide. Furthermore, enzymes are often more selective and more efficient catalysts than their chemical counterparts designed by man. For a more complete overview of the advantages of enzymatic catalysis, reference is made to Faber, *Biotransformations in Organic Chemistry*, 3rd ed., Springer-Verlag, New York, 1997.

In the fine chemical industry, optically pure halohydrins and epoxides are used as building blocks for various pharmaceutical products. Halohydrins are often considered as direct precursors for epoxides. Ring closure of an optically pure halohydrin generally leads to an optically pure epoxide. Recently, a kinetic resolution of a halohydrin containing an aromatic group, such as 2-chloro-1-phenylethanol, with a halohydrin dehalogenase from *Agrobacterium radiobacter* AD1 has been described (Lutje Spelberg et al., Tetrahedron: Asymmetry, 1999, 10, 2863).

The present invention provides a process wherein, optionally substituted, epoxides may be converted to alcohols in a highly enantioselective manner. It has been found that the desired enantioselectivity may be accomplished by enzymatically converting an optionally substituted epoxide of the formula

(I)

wherein $R_1$ is hydrogen or an, optionally substituted, aromatic or aliphatic group, to a mixture of an optically enriched epoxide of the formula (1) and an optically enriched alcohol of the formula

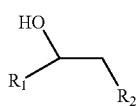

(II)

wherein $R_2$ is chosen from the group of I, Cl, Br, CN, $N_3$, $NO_2$, $NO_3$, SCN, OCN, OR', NHR', SR', SnR', SeR', PR' and $CO_2R'$, wherein R' is chosen from hydrogen, amino groups, hydroxyl groups, alkyl groups, aryl groups, aralkyl, alkenyl and cycloalkyl groups, which process comprises reacting the epoxide with an anionic nucleophile ($R_2^-$) in the presence of a halohydrin dehalogenase.

Surprisingly, it has been found that by converting an epoxide according to the invention a very high enantiomeric excess may be obtained. Even when the starting material is a racemic mixture of both enantiomers of the epoxide, mainly, if not only, one of the possible enantiomers of the product is obtained. Accordingly, the invention enables not only a very enantioselective manner of producing an alcohol, but also an enantioselective kinetic resolution of the epoxide. For instance, in case of a reaction of (substituted) styrene oxides with an aside, the (R)-enantiomer of the azidoalcohol is mainly formed, leaving behind the non-reacted (S)-enantiomer of the epoxide.

Moreover, the present process is highly regiospecific. Upon ring-opening of the epoxide, two different products may be formed: one in which the —OH group is present at the carbon atom adjacent to the $R_1$ group, and one in which the —OH group is present at the carbon atom on the distal end from the $R_1$ group. In a process according to the invention, mainly, if not only, the isomer with the —OH group at the carbon atom adjacent to the $R_1$ is formed.

The product of the reaction, the alcohol with the formula (II), is a building block for a wide variety of pharmaceutical compounds. For example, 2-azido-1-phenylethanol, which may be formed by the enzymatic reaction of sodium azide and styrene oxide, can be converted to biologically active 2-aminophenyl ethanol by catalytic hydrogenation.

In principle, any kind of epoxide may be converted in accordance with the invention. As mentioned, the $R_1$ group is hydrogen or an, optionally substituted, aromatic or aliphatic group, which preferably contains from 1 to 20 carbon atoms. Preferably, $R_1$ is chosen from the group of optionally substituted alkyl, aryl, aralkyl, alkenyl, cycloalkyl, and alkoxy groups.

Preferred examples of the alkyl group represented by $R_1$ include straight or branched alkyl groups having 1 to 15 carbon atoms such as a methyl group, ethyl group, propyl group, isopropyl group, butyl group, pentyl group, hexyl group, heptyl group or dodecyl group. Representative epoxides from this group include 1,2-epoxy propane, 1,2-epoxy-3-methylpentane and 1,2-epoxy hexane. The alkyl group can have substituents such as a halogen atom, leading to for example epichlorohydrin, epifluorohydrin or epibromohydrin. The alkyl group can have a substituent such as an hydroxyl group, for example glycidol. The alkyl group can have a unsubstituted or substituted amino group such as amino, methylamino or dimethylamino. Examples of aryl groups represented by $R_1$ include phenyl and naphtyl groups.

Styrene oxide or styrene oxides having a substituent or multiple substituents on the aromatic ring are examples of the phenyl group. Representative examples of epoxides are styrene oxide, 4-nitrostyrene oxide, 2-nitrostyrene oxide, 3-nitrostyrene oxide, 3-chlorostyrene oxide, 4-chlorostyrene oxide or 2,3-dichlorostyrene oxide. Examples of aralkyl groups represented by $R_1$ include a benzyl group, 2-phenylethyl group and a 1-naphtylmethyl group. Examples of alkenyl groups represented by $R_1$ include a vinyl group, allyl group and 5-hexenyl group. Examples of cycloalkyl groups represented by $R_1$ include a cyclopropyl group, cyclobutyl group, cyclopentyl group and cyclohexyl group. Examples of alkoxy groups represented by $R_1$ include a phenoxy group, 4-nitrophenoxy group, napthyloxy group, methoxy group, hexyloxy group and vinyloxy group.

A preferred class of epoxides that may be converted has the following formula:

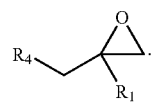

(III)

This class of epoxides may be substituted at the carbon atom bearing the $R_1$ group by a —$CH_2R_4$ group, wherein the $R_4$ group may be independently chosen from Cl, Br and I. Preferred examples of this class of epoxides are epichlorohydrin, epibromohydrin and 2-(chloromethyl)-2-methyloxirane. It has been found that during conversion to an alcohol, particularly when azide is used as the nucleophile, the enantionmer of the epoxide which is not converted is racemized. Due to this racemization a total conversion of epichlorohydrin is achieved and the product is obtained in high optically purity. Normally, in a kinetic resolution the maximum yield of the product is limited to 50%, but due to the racemization a yield of higher than 50% can be achieved. Another advantage of this process, besides the increased yield, is a much simpler product recovery since a separation of the product from the remaining substrate is not necessary.

In another preferred embodiment, the epoxide is a stryrene oxide, which may or may not be substituted. When this conversion is carried out chemically, i.e., in the absence of a halohydrin dehalogenase according to the invention, the product obtained will be a mixture of two compounds having their alcohol functionality on their carbon atom α or β to the aromatic ring. For example, the non-catalyzed chemical ring opening of styrene oxide by sodium azide will yield a mixture of regio-isomers with the alcohol functionality on the α and on the β-position in a molar ratio of 2:98 (α:β). Surprisingly, when a styrene oxide is converted in accordance with the invention, the other regio-isomer (i.e., wherein the alcohol functionality is present at the carbon atom α to the aromatic ring. The carbon atom a to the aromatic ring is the carbon atom within the epoxide ring which bears the aromatic ring substituent.) is obtained selectively. As separation of the two possible regio-isomers is very difficult, this regiospecificity is a great advantage of the invention.

Particularly preferred is an embodiment wherein the epoxide has the formula:

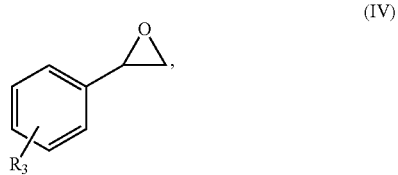

(IV)

wherein R₃ is an ortho-, meta-, or para-substituent chosen from the group of —NO₂, —NH₂, —CH₃, —OCH₃, —OCH₂CH₃, —OH, —F, —Cl, —Br, —I, —COOH and —CN. It has been found that the regiospecificity is particularly high for the conversion of these epoxides.

The epoxide can be present in solubilized form in a concentration of 1 to 300 mM or as a second solid or liquid phase in concentration up to 300 mM in the reaction medium. The epoxide itself can be the second phase or it can be dissolved in a second organic phase. This can be done by dissolving the epoxide in an organic solvent which is immiscible with water, such as hexane or octane. The obtained solution is then brought into contact with the aqueous phase containing the enzyme and the two phases are vigorously mixed. The use of such a second phase has the advantage that the separation of the epoxide and the alcohol after the reaction can be simplified. Generally, the alcohol is expected to remain solubilized in the aqueous phase and the epoxide can typically be recovered from the organic phase. Preferably, the epoxide is prior to its conversion brought in an aqueous medium in which it will preferably be present in an amount of 0.01 to 20 wt %, based on the combined weights of the aqueous medium and the epoxide.

The nature of the nucleophile chosen to convert the epoxide in a process according to the invention will normally depend on the nature of the objective product. Suitable nucleophiles include of I, Cl, Br, CN, N₃, NO₂, NO₃, SCN, OCN, OR', NHR', SR', SnR', SeR', PR' and CO₂R', wherein R' is chosen from hydrogen, amino groups, hydroxyl groups, alkyl groups, aryl groups, aralkyl, alkenyl and cycloalkyl groups. Of course, substituted alkyl groups, aryl groups, aralkyl, alkenyl and cycloalkyl groups are also encompassed. When R' is an alkyl group, it preferably contains from 1 to 15 more preferably from 1 to 6 carbon atoms. When R' is an aryl group, it preferably is a phenyl or a naphtyl group. Preferred aralkyl groups which may be represented by R' include benzyl, 2-phenylethyl and 1-naphtylmethyl groups. Preferred alkenyl groups from which R' may be chosen are vinyl and allyl groups. When R' is a cycloalkyl group, it may suitably have from 3 to 12 carbon atoms. Preferred cycloalkyl groups are cyclopropyl, cyclobutyl, cyclopentyl, and cyclohexyl.

Preferably, particularly when the epoxide is a styrene oxide or a substituted styrene oxide, the nucleophile is NO₂⁻ or N₃⁻. The nucleophile may be employed in the form of a salt, for instance as a sodium or potassium salt. An excess of the nucleophilic reagent may lead to the non-enantioselective formation of the unwanted regio-isomer of the objective product. This may be circumvented by either performing the reaction on a shorter time-scale, performing the reaction at a lower temperature, employing a larger quantity of the enzyme, or by adding the nucleophilic reagent to the reaction mixture in a slower fashion. Typically, the nucleophile will be used in an amount of 0.6 to 100 molar equivalents with respect to the epoxide, depending on the position of the equilibrium between the epoxide and the alcohol. For example, in the case of sodium azide as the nucleophile 0.6 molar equivalents suffice to achieve a substantially completed kinetic resolution since the position of the equilibrium favors the formation of the alcohol over the epoxide. In the case of sodium chloride as the nucleophile, an excess (50-100 molar equivalents) are preferably added to favor the formation of the alcohol.

It is preferred that the reaction is carried out in a buffered aqueous medium to which the epoxide is solubilized or is added as a second solid or liquid phase. Suitable buffers are for example Tris-buffer (2-amino-2-(hydroxymethyl)-1,3-propanediol adjusted to a desired pH with H₂SO₄), glycine-buffer (glycine adjusted to a desired pH by NaOH), phosphates buffer or MOPS buffer (4-morpholinepropanesulfonic acid adjusted to a desired pH with NaOH). These are preferably used a concentration of 50 to 250 mM.

Optionally, co-solvents like dimethyl sulfoxide, tetrahydrofuran or acetonitrile may be added to increase the solubility of the epoxide. Co-solvents may be added in amounts of 5 vol % up to 50 vol %. An increasing percentage of co-solvent may favor the solubility of the epoxide. However, a disadvantageous inactivation of the enzyme can be observed at higher co-solvent concentrations.

The pH of the medium preferably lies between 3 and 12, more preferably between 6.5 and 8. The temperature at which the reaction is carried out preferably lies between 0° C. to 60° C., more preferably between 20° C. and 30° C.

The enzyme used is a halohydrin dehalogenase. A highly suitable halohydrin dehalogenase is a polypeptide having an amino acid sequence as shown in SEQ ID NO:2 or a homologue or functional derivative thereof. In the context of the invention, the term "a homologue" refers to a sequence which is at least for 90% homologous, and preferably at least 90% identical, to the sequence of which it is a homologue. A functional derivative is a polypeptide which has undergone a minor derivatization or modification substantially without adversely affecting the enzymatic and catalytic properties of the polypeptide. Suitable examples of enzymes that can be used are halohydrin dehalogenase of *Agrobacterium radiobacter* (CBS 750.97), *Mycobacterium* sp. strain GP1 (Poelarends et al. J. Bacteriol., 1999, 181, 2050) or *Arthrobacter* sp. strain AD2 (van den Wijngaard et al., J. Bacteriol., 1991, 124). Particular good results have been obtained using a halohydrin dehalogenase derived from *Agrobacterium radiobacter* strain AD1 deposited at the Centraal Bureau voor de Schimmelcultures on May 7, 1997 under deposit number CBS 750.97. Another enzyme obtained from this organism has been described extensively in the International Patent Application 98/53081 for its epoxide hydrolase activity.

It is to be noted that an enzyme used according to the invention, a halohydrin dehalogenase, should be distinguished from epoxide hydrolases. The latter have been described extensively in Archer, Tetrahedron, 53 (1997), pp. 15617-15662. The only feature that both types of enzymes may have in common is that they can be isolated from *Agrobacterium radiobacter* strain AD1. Likewise, Lutje Spelberg et al., Tetrahedron: Asymmetry, 9 (1998), pp. 459-466 and European Patent Application 0879890 relate to applications of an epoxide hydrolase.

The enzyme can be added as whole cells, in lyophilized form as a crude extract or as a purified enzyme. The enzyme can be immobilized on a macroscopic carriers such as cellulose, sephadex, or dextran. The enzyme can also be applied as crosslinked enzyme crystals (CLEC's) or entrapped in reversed micelles. In a typical experiment, an enzyme solution is mixed with a buffer solution containing a nucleophile and an epoxide. Optionally, additives such as mercaptoethanol or glycerol can be added to the reaction mixture to stabilize the enzyme.

After the reaction the whole reaction mixture can be extracted using organic solvents such as diethylether, ethyl acetate, dichloromethane or toluene. The epoxide and the alcohol can subsequently be separated by techniques such as crystallisation (in the case of solid substances), fraction distillation or flash chromatography on silica 60H using for example heptane/ethylacetate (ratio 7:3) as eluent. The enantiomeric composition of the epoxides and alcohols can be determined using chiral gas chromatography or chiral HPLC.

The invention will now be further elucidated by the following, non-restrictive examples.

3. EXAMPLES

Example 1

A gene library of *A. radiobacter* AD1 was constructed in the cosmid vector pLAFR3. After in vitro packaging, the library was transduced to *E. coli* HB101. Transconjugants were screened for dehalogenase activity with 1,3-dichloro-2-propanol. The halohydrin dehalogenase gene, designated hheC, was sequenced and subsequently amplified by PCR and cloned behind the T7 promoter of the expression vector pGEF$^+$, yielding pGEFhheC. The halohydrin dehalogenase gene was overexpressed up to 30% of soluble protein by introduction of pGEFhheC in *E. coli* BL21 (DE3). HheC has the sequence shown as SEQ ID NO:1.

For the described kinetic resolutions purified enzyme was used. Plasmid DNA was transformed by electroporation to competent *E. coli* BL21 (DE3) cells, which were then plated out on LB medium containing tetracycline and incubated overnight at 30° C. A preculture was started by inoculating 100 ml of LB medium containing tetracycline with the transformants from a plate to a initial $OD_{600}$ of 0.1. The culture was incubated at 30° C. until an $OD_{600}$ of 1-2 was reached, diluted in 1 liter of LB medium containing tetracycline and incubated overnight at 20° C. The cells were subsequently centrifuged, washed and resuspended. A crude extract was prepared by ultrasonic disruption and centrifugation of the cells. This was followed by a purification step with a Resource Q column yielding the enzyme having SEQ ID NO:2.

The above procedure is analogous to a procedure which has been described in more detail in the International Patent Application 98/53081, where the enzyme that was prepared was an epoxide hydrolase. The description of the recombinant preparation of the enzyme of said international patent application is to be considered incorporated herein by reference.

The activity of chimeric fusions, Pfu-Pae3192 with and without the His-tag were compared. Preliminary results indicate that the non His-tagged version exhibited up to 50-fold less activity when compared to the His-tagged version.

Example 2

To 15 ml of Tris-$SO_4$ buffer (50 mM, pH=7.3) containing 2 mM of para-nitro styrene oxide and 10 mM of $NaN_3$, 2.8 mg of purified enzyme, obtained according to Example 1, was added. The reaction was monitored by periodically taking 200 µl samples and extracting them with 2 ml of diethylether. The reaction was stopped when an e.e. of higher than 99% of the remaining enantiomer was reached and the solution was twice extracted with diethylether. The organic phase was analysed by chiral HPLC using a chiralpak AS column from Daicel. The remaining (S)-para-nitro styrene oxide was obtained with an e.e. >99% and the product (R)-2-azido-1-(para-nitro-phenyl)-ethanol with an e.e. of 94%. The corresponding E-value was calculated to be higher than 200 from the e.e.'s of the epoxide and the azido alcohol (Straathof et al., Enzyme Microb. Technol. 1997, 21, 559). The other regio-isomer 2-azido-2-(para-nitro-phenyl)-ethanol was also formed due to a chemical side reaction in a ratio of 1:12 compared to (R)-2-azido-1-(para-nitro-phenyl)-ethanol.

Example 3

To 1 ml of Tris-$SO_4$ buffer (50 mM, pH=7.3) containing 0.25 mM of para-nitro styrene oxide and 0.5 mM of $NaN_3$, 0.7 mg of purified enzyme, obtained according to Example 1, was added. The reaction was stopped after 15 min and the solution was extracted with diethylether. The organic phase was analysed by chiral HPLC. The remaining (S)-para-nitro styrene oxide was obtained with an e.e. >99% and the product (R)-2-azido-1-(para-nitro-phenyl)-ethanol with an e.e. of 96%. The other regio-isomer 2-azido-2-(para-nitro-phenyl)-ethanol was formed in a ratio of 1:217 compared to (R)-2-azido-1-(para-nitro-phenyl)-ethanol. From this we concluded that the enzymatic azidolysis is almost absolutely regioselective (β selectivity>99%). The observed lower regioselectivity during a kinetic resolution on a longer time scale was due to the unwanted chemical side reaction.

Example 4

To 60 ml of MOPS buffer (50 mM, pH=7.0), 0.47 gram (3.2 mmol) of racemic para-nitro styrene oxide was added and the suspension was stirred for 60 min. The halohydrin dehalogenase, obtained as described in Example 1, (29 mg in 6 ml buffer) was added. A prepared stock solution of 0.12 gram (1.6 mmol) $NaN_3$ in 5 ml MOPS buffer was slowly added over a period of 24 hours. The reaction was stopped and the suspension was three times extracted with diethylether. After separating, the organic phase was dried with $MgSO_4$, and removed by rotary evaporator yielding an orange oil. This mixture was redissolved in diethylether and the composition and e.e. of the products were determined by chiral HPLC. The mixture mainly consisted of (S)-para-nitro styrene oxide in 46% yield (98% e.e.) and (R)-2-azido-1-(para-nitrophenyl)ethanol in 47% yield (97% e.e.). The chemical side product 2-azido-2-(para-nitrophenyl)ethanol was formed to a total of 4% of the reaction mixture. The product of chemical hydrolysis of the epoxide, para-nitrophenyl ethanediol was formed in 3%. All the mentioned yields are calculated yields. Flash chromatography on silica 60H using heptane/ethylacetate (ratio 7:3) as eluent yielded pure epoxide and azido alcohols. The NMR data were identical with synthesized racemic reference compounds.

Example 5

To 20 ml of Tris-$SO_4$ buffer (50 mM, pH=7.3) containing 2 mM of para-chlorostyrene oxide and 1.2 mM of $NaN_3$, 1.0 mg of purified enzyme, obtained as described in Example 1, was added. At 55% conversion, reaction was stopped and the solution was extracted with diethylether. The organic phase was analysed by chiral GC. The remaining (S)-para-chloro styrene oxide was obtained with an e.e. of higher than 99% and (R)-2-azido-1-(para-chloro-phenyl)-ethanol with an e.e. of 98%.

Example 6

To 20 ml of Tris-SO$_4$ buffer (50 mM, pH=7.3) containing 2 mM of para-chlorostyrene oxide and 1.2 mM of NaNO$_2$, 1.0 mg of purified enzyme, obtained as described in Example 1, was added. At 58% conversion, reaction was stopped and the solution was extracted with diethylether. The organic phase was analysed by chiral GC. The remaining (S)-para-chloro styrene oxide was obtained with an e.e. of higher than 99%.

Example 7

To 20 ml of Tris-SO$_4$ buffer (50 mM, pH=7.3) containing 20 mM of epichlorohydrin and 20 mM of NaN$_3$, 1.0 mg of purified enzyme was added. At 66% conversion, reaction was stopped and the solution was extracted with diethylether. The organic phase was analyzed by chiral GC. Besides the remaining epichlorohydrin, the mixture consisted of 1-azido-3-chloro-2-propanol in 92% e.e., 2-azidomethyl-oxirane in 92% e.e. and the non-chiral 1,3-dichloro-2-propanol.

Example 8

To 20 ml of Tris-SO$_4$ buffer (50 mM, pH 7.3) containing 20 mM of epichlorohydrin and 20 mM of NaN$_3$, 1.0 mg of purified enzyme was added. At total conversion of epichlorohydrin, the reaction was stopped and the solution was extracted with diethylether. The organic phase was analysed by chiral GC. The product consisted of a mixture of 1-azido-3-chloro-2-propanol in 92% e.e. and 2-azidomethyl-oxirane in 92% e.e. (Addition of a small amount of an NaOH gave 2-azidomethyl-oxirane as a single product in 92% e.e.).

Example 9

To 20 ml of Tris-SO$_4$ buffer (50 mM, pH=6.5) containing 20 mM of epibromohydrin, 30 mM of NaN$_3$, 50 mM NaBr, 1.0 mg of purified enzyme was added. After completion of the reaction, the mixture obtained was extracted with diethylether and the organic phase was analyzed by chiral GC. The product 1-azido-3-bromo-2-propanol Was obtained in >99% e.e. and 75% yield.

SEQ ID NO 1: DNA Sequence of the Halohydrin Dehalogenase Gene from AD1 (Capitals Only)

```
taaaatctcggcaaatatctagcgatcataggatataaaggatctgagtA
TGTCAACCGCAATTGTAACAAACGTTAAGCATTTTGGGGGAATGGGGTCT
GCACTTCGTCTCTCGGAAGCAGGACATACAGTGGCTTGCCACGATGAAAG
CTTCAAACAAAAGGACGAACTTGAAGCCTTTGCCGAAACCTATCCACAAC
TCAAACCAATGTCGGAACAAGAACCAGCGGAACTCATCGAGGCAGTTACC
TCCGCTTATGGTCAAGTTGATGTACTTGTGAGCAACGACATATTCGCACC
AGAGTTCCAACCCATAGATAAATACGCTGTAGAGGACTATCGCGGTGCGG
TCGAGGCGCTACAAATTAGACCATTTGCACTGGTCAACGCCGTTGCAAGT
CAAATGAAGAAGCGCAAAAGCGGACATATTATCTTTATTACCTCTGCAAC
GCCCTTCGGGCCTTGGAAGGAACTTTCTACCTACACGTCAGCCCGAGCAG
GTGCATGCACCTTGGCAAATGCCCTTTCGAAGGAACTCGGTGAATACAAC
ATTCCGGTGTTCGCAATAGGACCCAATTATCTTCACAGTGAAGATAGTCC
CTACTTCTACCCCACAGAACCGTGGAAAACGAATCCAGAACACGTTGCCC
ATGTCAAAAAAGTCACTGCGCTCCAGCGGTTAGGTACACAGAAAGAATTG
GGAGAACTCGTCGCGTTTCTCGCGTCTGGTAGTTGTGACTATCTGACCGG
CCAGGTGTTCTGGTTGGCCGGCGGATTCCCAATGATCGAGCGTTGGCCTG
GTATGCCCGAGTAGgaccggagtgagaactctcttcaagactgcttgcag
ttttggattgccgcgggacagacgttttgc
```

SEQ ID NO 2: Amino Acid Sequence of HheC

```
MSTAIVTNVKHFGGMGSALRLSEAGHTVACHDESFKQKDELEAFAETYPQ
LKPMSEQEPAELIEAVTSAYGQVDVLVSNDIFAPEFQPIDKYAVEDYRGA
VEALQIRPFALVNAVASQNKKRKSGHIIFITSATPFGPWKELSTYTSARA
GACTLANALSKELGEYNIPVFAIGPNYLHSEDSPYFYPTEPWKTNPEHVA
HVKKVTALQRLGTQKELGELVAFLASGSCDYLTGQVFWLAGGFPMIERWP
GMPE
```

---

What is claimed is:

1. A process for enzymatically converting an optionally substituted, epoxide of formula (I),

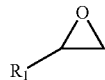

(I)

wherein R$_1$ is an optionally substituted, aromatic or aliphatic group, to a mixture of an optically enriched epoxide of formula (I) and an optically enriched alcohol of formula (II),

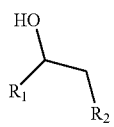

(II)

wherein R$_2$ is chosen from the group consisting of N$_3$, NO$_2$, SCN, OCN, and R'CO$_2$, wherein R' is chosen from the group consisting of hydrogen, alkyl groups, aryl groups, aralkyl, alkenyl and cycloalkyl groups, which process comprises reacting the epoxide with an anionic nucleophile of (R$_2$) in the presence of a halohydrin dehalogenase.

2. The process according to claim 1, wherein the optically enriched alcohol is recovered.

3. The process according to claim 1, wherein the optically enriched epoxide is recovered.

4. The process according to claim 1, wherein the epoxide is converted from a mixture comprising both enantiomers of said epoxide.

5. The process according to claim 4, wherein the mixture is a racemic mixture.

6. The process according to claim 1, wherein the halohydrin dehalogenase is a halohydrin dehalogenase of *Agrobacterium radiobacter* (CBS 750.97), *Arthrobacter* sp. strain AD2 or *Mycobacterium* sp. strain GP 1.

7. The process according to claim 1, wherein the halohydrin dehalogenase has an amino acid sequence that is at least 90% identical to SEQ ID NO:2.

8. The process according to claim 1, wherein the halohydrin dehalogenase has the amino acid sequence of SEQ ID NO:2.

9. The process according to claim 1, wherein R$_1$ is chosen from the group consisting of optionally substituted alkyl, aryl, aralkyl, cycloalkyl, and alkoxy groups.

10. The process according to claim 9, wherein the substitution on R$_1$ is chosen from the group consisting of amino groups, halogens, hydroxyl groups, cyano groups, azide groups, nitro groups, haloalkyl groups, acyl groups, alkoxy groups, phenoxy groups, and carboxyl groups.

11. The process according to claim 1, wherein the epoxide is present in an aqueous medium in an amount of from 0.01 to 20 wt. %, based on the combined weights of the aqueous medium and the epoxide.

12. The process according to claim 1, wherein the temperature is between 0 and 60° C.

13. The process according to claim 1, wherein the pH is between 3 and 12.

14. A process for enzymatically converting an optionally substituted epoxide of formula (I),

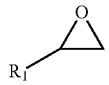

(I)

wherein R$_1$ is an optionally substituted aromatic group, to a mixture of an optically enriched epoxide of formula (I) and an optically enriched alcohol of the formula (II),

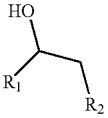

(II)

wherein R$_2$ is chosen from the group consisting of CN, N$_3$, NO$_2$, SCN, OCN, and R'CO$_2$, wherein R' is chosen from the group consisting of hydrogen, alkyl groups, aryl groups, aralkyl, alkenyl and cycloalkyl groups, which process comprises reacting the epoxide with an anionic nucleophile of (R$_2$) in the presence of a halohydrin dehalogenase.

15. The process according to claim 14, wherein the epoxide has the formula (IV),

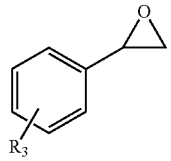

(IV)

wherein R$_3$ is an ortho-, meta-, or para-substituent chosen from the group consisting of —NO$_2$, —NH$_2$, —CH$_3$, —OCH$_3$, —OCH$_2$CH$_3$, —OH, —F, —Cl, —Br, —I, —COOH and —CN.

16. The process according to claim 14, wherein the anionic nucleophile is N$_3$—, NO$_2$—, or CN—.

17. The process according to claim 14, wherein the optically enriched alcohol is recovered.

18. The process according to claim 14, wherein the optically enriched epoxide is recovered.

19. The process according to claim 14, wherein the epoxide is converted from a mixture comprising both enantiomers of said epoxide.

20. The process according to claim 19, wherein the mixture is a racemic mixture.

21. The process according to claim 14, wherein the halohydrin dehalogenase is halohydrin dehalogenase of *Agrobacterium radiobacter* (CBS 750.97), *Arthrobacter* sp. strain AD2 or *Mycobacterium* sp. strain GP 1.

22. The process according to claim 14, wherein the halohydrin dehalogenase has an amino acid sequence that is at least 90% identical to SEQ ID NO:2.

23. The process according to claim 14, wherein the halohydrin dehalogenase has the amino acid sequence of SEQ ID NO:2.

24. The process according to claim 14, wherein $R_1$ is chosen from the group consisting of optionally substituted alkyl, aryl, aralkyl, cycloalkyl, and alkoxy groups.

25. The process according to claim 24, wherein the optional substituent on $R_1$ is chosen from the group consisting of amino groups, halogens, hydroxyl groups, cyano groups, azide groups, nitro groups, haloalkyl groups, acyl groups, alkoxy groups, phenoxy groups, and carboxyl groups.

26. The process according to claim 14, wherein the epoxide is present in an aqueous medium in an amount of from 0.01 to 20 wt. %, based on the combined weights of the aqueous medium and the epoxide.

27. The process according to claim 14, wherein the temperature is between 0 and 60° C.

28. The process according to claim 14, wherein the pH is between 3 and 12.

* * * * *

SEQUENCE LISTING

```
<160> NUMBER OF SEQ ID NOS: 2

<210> SEQ ID NO 1
<211> LENGTH: 878
<212> TYPE: DNA
<213> ORGANISM: Agrobacterium radiobacter

<400> SEQUENCE: 1
taaaatctcg gcaaatatct agcgatcata ggatataaag gatctgagta tgtcaaccgc      60
aattgtaaca aacgttaagc attttggggg aatgggtct gcacttcgtc tctcggaagc     120
aggacataca gtggcttgcc acgatgaaag cttcaaacaa aaggacgaac ttgaagcctt    180
tgccgaaacc tatccacaac tcaaaccaat gtcggaacaa gaaccagcgg aactcaccga   240
```

-continued

```
ggcagttacc tccgcttatg gtcaagttga tgtactgtga gcaacgacat attcgcacca    300
gagttccaac ccatagataa atacgctgta gagactatcg cggtgcggtc gaggcgctac    360
aaattagacc atttgcactg gtcaacgccg ttgcaagtca aatgaagaag cgcaaaagcg    420
gacatattat ctttattacc tctgcaacgc ccttcgggcc ttggaaggaa ctttctacct    480
acacgtcagc ccgagcaggt gcatgcacct tggcaaatgc cctttcgaag gaactcggtg    540
aatacaacat tccggtgttc gcaataggac ccaattatct tcacagtgaa gatagtccct    600
acttctaccc cacagaaccg tgaaaaacga atccagaaca cgttgcccat gtcaaaaaag    660
tcactgcgct ccagcggtta ggtacacaga aagaattggg agaactcgtc gcgtttctcg    720
cgtctggtag ttgtgactat ctgaccggcc aggtgttctg gttggccggc ggattcccaa    780
tgatcgagcg ttggcctggt atgcccgagt aggaccggag tgagaactct cttcaagact    840
gcttgcagtt ttggattgcc gcgggacaga cgttttgc                            878
```

<210> SEQ ID NO 2
<211> LENGTH: 254
<212> TYPE: PRT
<213> ORGANISM: Agrobacterium radiobacter

<400> SEQUENCE: 2

```
Met Ser Thr Ala Ile Val Thr Asn Val Lys His Phe Gly Gly Met Gly
  1               5                  10                  15

Ser Ala Leu Arg Leu Ser Glu Ala Gly His Thr Val Ala Cys His Asp
             20                  25                  30

Glu Ser Phe Lys Gln Lys Asp Glu Leu Glu Ala Phe Ala Glu Thr Tyr
         35                  40                  45

Pro Gln Leu Lys Pro Met Ser Glu Gln Glu Pro Ala Glu Leu Ile Glu
     50                  55                  60

Ala Val Thr Ser Ala Tyr Gly Gln Val Asp Val Leu Val Ser Asn Asp
 65                  70                  75                  80

Ile Phe Ala Pro Glu Phe Gln Pro Ile Asp Lys Tyr Ala Val Glu Asp
                 85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```